(12) United States Patent
Forsell (10) Patent No.: US 12,151,082 B2
(45) Date of Patent: *Nov. 26, 2024

(54) IMPLANTABLE INFUSION DEVICES AND METHODS

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 136 days.

This patent is subject to a terminal disclaimer.

(21) Appl. No.: 17/944,209

(22) Filed: Sep. 14, 2022

(65) Prior Publication Data

US 2023/0014979 A1    Jan. 19, 2023

Related U.S. Application Data (63) Continuation of application No. 15/362,837, filed on Nov. 29, 2016, now Pat. No. 11,446,432, which is a
(Continued)

(51) Int. Cl.
*A61M 5/142* (2006.01)
*A61B 17/32* (2006.01)
(Continued)

(52) U.S. Cl.
CPC .... *A61M 5/14276* (2013.01); *A61M 5/14224* (2013.01); *A61M 5/1428* (2013.01); *A61M 5/158* (2013.01); *A61M 5/16818* (2013.01); *A61M 5/172* (2013.01); *A61M 5/1723* (2013.01); *A61B 17/32* (2013.01); *A61M 2005/14208* (2013.01); *A61M 2005/14252* (2013.01); *A61M 2005/14284* (2013.01); *A61M 5/3291* (2013.01); *A61M 25/0084* (2013.01); *A61M 2025/009* (2013.01); *A61M 2205/0211* (2013.01); *A61M 2205/073* (2013.01);
(Continued)

(58) Field of Classification Search
None
See application file for complete search history.

(56) References Cited

U.S. PATENT DOCUMENTS

3,598,287 A * 8/1971 de Man ............... B67D 1/0412
222/38
3,692,027 A * 9/1972 Ellinwood, Jr. .. A61M 5/14276
604/502
(Continued)

*Primary Examiner* — Scott J Medway (57) ABSTRACT

Infusion devices and methods are provided for a drug delivery system and can include an infusion needle (1) having a tip end (2) and a drive unit (D) coupled to the infusion needle and arranged for advancing the tip end of the infusion needle to penetrate any fibrosis when the infusion device is implanted in a patient's body. The infusion needle and drive unit are designed for implantation in a patient's body. Other components of the drug delivery system may be part of the implantable infusion device or, alternatively, be for extracorporal use cooperating with the implanted infusion device. Preferably, the infusion needle can be advanced and retracted with each infusion cycle. Furthermore, upon each advancement and/or retraction, the needle may be moved laterally so as to vary the injection site. Needle (1) and drive unit (D) are preferably disposed within a body (15), with the infusion needle being arranged for penetrating a self-sealing penetration membrane (18).

20 Claims, 6 Drawing Sheets

Related U.S. Application Data continuation of application No. 11/591,292, filed on Nov. 1, 2006, now Pat. No. 9,504,785.

(60) Provisional application No. 60/732,740, filed on Nov. 2, 2005.

(51) Int. Cl.
*A61M 5/158* (2006.01)
*A61M 5/168* (2006.01)
*A61M 5/172* (2006.01)
*A61M 5/32* (2006.01)
*A61M 25/00* (2006.01)

(52) U.S. Cl.
CPC . *A61M 2205/075* (2013.01); *A61M 2205/106* (2013.01); *A61M 2205/128* (2013.01); *A61M 2205/192* (2013.01); *A61M 2205/3306* (2013.01); *A61M 2205/3317* (2013.01); *A61M 2205/3334* (2013.01); *A61M 2205/3337* (2013.01); *A61M 2205/3389* (2013.01); *A61M 2205/3523* (2013.01); *A61M 2205/3569* (2013.01); *A61M 2205/8206* (2013.01); *A61M 2205/8237* (2013.01); *A61M 2210/1021* (2013.01); *A61M 2210/1042* (2013.01); *A61M 2210/1078* (2013.01); *A61M 2210/12* (2013.01); *A61M 2230/20* (2013.01); *A61M 2230/201* (2013.01); *A61M 2230/208* (2013.01)

(56) References Cited

U.S. PATENT DOCUMENTS

| | | | | |
|---|---|---|---|---|
| 3,731,681 A * | 5/1973 | Blackshear | A61M 5/141 | 604/141 |
| 3,923,060 A * | 12/1975 | Ellinwood, Jr. | A61B 5/021 | 128/DIG. 13 |
| 4,003,379 A * | 1/1977 | Ellinwood, Jr. | A61M 5/14532 | 128/DIG. 1 |
| 4,221,219 A * | 9/1980 | Tucker | A61M 5/14276 | 604/141 |
| 4,265,241 A * | 5/1981 | Portner | A61M 5/14276 | 604/141 |
| 4,274,407 A * | 6/1981 | Scarlett | A61M 5/148 | 604/153 |
| 4,563,175 A * | 1/1986 | LaFond | A61M 5/1456 | 604/246 |
| 4,628,928 A * | 12/1986 | Lowell | A61M 5/14276 | 606/1 |
| 4,886,499 A * | 12/1989 | Cirelli | A61M 5/142 | 604/141 |
| 4,902,279 A * | 2/1990 | Schmidtz | A61M 5/2033 | 604/137 |
| 4,944,728 A * | 7/1990 | Carrell | A61M 25/0606 | 604/110 |
| 5,358,474 A * | 10/1994 | Kaldany | A61M 37/0069 | 604/502 |
| 5,441,499 A * | 8/1995 | Fritzsch | A61B 17/00234 | 606/45 |
| 5,518,499 A * | 5/1996 | Agar | A61F 2/26 | 600/40 |
| 5,665,065 A * | 9/1997 | Colman | A61M 5/1723 | 604/67 |
| 5,690,108 A * | 11/1997 | Chakeres | A61B 6/0442 | 378/205 |
| 5,713,946 A * | 2/1998 | Ben-Haim | A61B 5/6885 | 607/122 |
| 5,814,020 A * | 9/1998 | Gross | A61M 5/14593 | 604/141 |
| 5,845,646 A * | 12/1998 | Lemelson | A61M 25/0068 | 604/21 |
| 5,865,227 A * | 2/1999 | Carilli | A61M 5/322 | 141/2 |
| 5,928,195 A * | 7/1999 | Malamud | A61M 5/14593 | 604/141 |
| 5,997,501 A * | 12/1999 | Gross | A61M 5/14248 | 604/65 |
| 6,003,736 A * | 12/1999 | Ljunggren | A61M 5/14566 | 222/386 |
| 6,004,269 A * | 12/1999 | Crowley | A61B 8/445 | 600/374 |
| 6,058,323 A * | 5/2000 | Lemelson | A61B 17/320758 | 600/408 |
| 6,077,215 A * | 6/2000 | Leysieffer | H04R 25/606 | 600/25 |
| 6,102,850 A * | 8/2000 | Wang | A61B 34/30 | 600/102 |
| 6,102,887 A * | 8/2000 | Altman | A61M 25/0147 | 604/95.01 |
| 6,113,574 A * | 9/2000 | Spinello | A61M 5/48 | 604/154 |
| 6,223,100 B1 * | 4/2001 | Green | H04N 13/296 | 348/E13.016 |
| 6,436,054 B1 * | 8/2002 | Viola | A61B 10/0275 | 600/562 |
| 6,475,139 B1 * | 11/2002 | Miller | A61B 1/00087 | 600/29 |
| 6,572,585 B2 * | 6/2003 | Choi | A61M 5/14244 | 604/151 |
| 6,589,229 B1 * | 7/2003 | Connelly | A61M 5/14248 | 604/890.1 |
| 6,602,241 B2 * | 8/2003 | Makower | A61M 25/065 | 604/509 |
| 6,685,648 B2 * | 2/2004 | Flaherty | A61M 5/007 | 600/463 |
| 6,740,075 B2 * | 5/2004 | Lebel | G06F 3/0673 | 604/151 |
| 6,936,003 B2 * | 8/2005 | Iddan | A61B 5/0031 | 600/101 |
| 6,948,918 B2 * | 9/2005 | Hansen | F16K 99/0015 | 604/153 |
| 7,043,295 B2 * | 5/2006 | Starkebaum | A61F 5/0026 | 607/40 |
| 7,066,922 B2 * | 6/2006 | Angel | A61M 5/1723 | 604/35 |
| 7,108,686 B2 * | 9/2006 | Burke | A61M 5/14593 | 604/145 |
| 7,250,037 B2 * | 7/2007 | Shermer | A61M 5/14248 | 604/134 |
| 7,320,700 B2 * | 1/2008 | Cooper | A61B 17/062 | 600/101 |
| 7,374,554 B2 * | 5/2008 | Menzi | A61M 25/0637 | 604/110 |
| 7,569,050 B2 * | 8/2009 | Moberg | A61M 5/1413 | 604/890.1 |
| 7,819,826 B2 * | 10/2010 | Diederich | A61B 18/04 | 601/3 |
| 7,828,771 B2 * | 11/2010 | Chiang | A61P 1/16 | 604/153 |
| 8,187,229 B2 * | 5/2012 | Weitzner | A61B 17/12136 | 604/95.01 |
| 2001/0041824 A1 * | 11/2001 | Zappala | A61F 2/26 | 604/502 |
| 2002/0040208 A1 * | 4/2002 | Flaherty | A61M 5/14248 | 604/67 |
| 2002/0055711 A1 * | 5/2002 | Lavi | A61M 5/326 | 604/110 |
| 2002/0095164 A1 * | 7/2002 | Andreas | A61B 17/3417 | 606/144 |
| 2002/0120263 A1 * | 8/2002 | Brown | A61N 1/06 | 606/41 |
| 2003/0014010 A1 * | 1/2003 | Carpenter | A61M 25/0084 | 604/95.04 |
| 2003/0050591 A1 * | 3/2003 | Patrick McHale | A61K 9/5068 | 604/4.01 |
| 2003/0069523 A1 * | 4/2003 | Williams | A61M 25/0113 | 600/585 |

(56) References Cited

U.S. PATENT DOCUMENTS

| | | | |
|---|---|---|---|
| 2003/0069541 A1* | 4/2003 | Gillis | A61M 39/0208 604/164.01 |
| 2003/0069547 A1* | 4/2003 | Gonon | A61M 25/0084 604/263 |
| 2003/0144648 A1* | 7/2003 | Forsell | A61F 2/004 604/246 |
| 2004/0097819 A1* | 5/2004 | Duarte | A61B 5/287 600/509 |
| 2005/0021023 A1* | 1/2005 | Guglielmi | A61B 17/12113 606/41 |
| 2008/0015445 A1* | 1/2008 | Saadat | A61B 5/6882 600/470 |
| 2008/0051718 A1* | 2/2008 | Kavazov | A61M 5/1413 604/93.01 |
| 2008/0319416 A1* | 12/2008 | Yodfat | A61M 5/422 604/513 |
| 2011/0196198 A1* | 8/2011 | Forsell | A61F 2/26 600/38 |
| 2011/0276037 A1* | 11/2011 | Forsell | A61M 5/1723 604/891.1 |

* cited by examiner

IMPLANTABLE INFUSION DEVICES AND METHODS

This application is a continuation of U.S. application Ser. No. 15/362,837, filed 29 Nov. 2016, which is a continuation of U.S. application Ser. No. 11/591,292, filed 1 Nov. 2006 and issued on Nov. 29, 2016 as U.S. Pat. No. 9,504,785, which claims the benefit of U.S. Provisional No. 60/732,740, filed on 2 Nov. 2005, the entire contents of each of which are hereby incorporated by reference.

BACKGROUND OF THE INVENTION

The present invention relates to an implantable infusion device and to a drug delivery system comprising both the implantable infusion device and at least one extracorporal component for cooperation from outside a patient's body with the implanted infusion device.

The infusion device according to the present invention is particularly suitable for long term applications, i.e. for applications where the patient receives drugs by infusion at predetermined time intervals over months or years. This is typically the case with cytostatica treatment during chemo therapy, insulin treatment in case of diabetes, and the like.

In such long term treatments it is inconvenient for the patient to deliver the drug at regular time intervals through the skin into the blood veins or tissue by way of a syringe penetrating the skin. Also, this may cause severe skin irritation. While in some cases the syringe or delivery catheter may rest in place in the body tissue for days or weeks, this may cause fibrosis to grow and build up on the part of the needle within the patient's body including the needle's exit port, thereby clogging the exit port and preventing drug delivery. Similarly, where the syringe or delivery catheter rests in place in a patient's blood vessel for days or weeks, this may cause thrombophlebitis, which is a form of thrombosis caused by an inflammation within the blood vessel. Such thrombosis formation may clog not only the needle's exit port but also the entire blood vessel.

The use of implantable drug delivery devices for long term applications has also been suggested. While skin irritation is not a problem with these devices, they still suffer from the drawback of fibrosis and thrombosis forming and building up on the drug delivery exit port. Therefore, the long term use of such implantable devices is limited.

WO 2004/012806 A1 discloses an apparatus for distributing liquid in a patient's body comprising an implantable pump adapted to pump the liquid and an implantable valve device adapted to direct the liquid pumped by the pump. Various applications are suggested, including the use of the apparatus as a drug delivery device. The valve members of the valve device are made from ceramic material for it provides excellent sealing properties and long term reliability if arranged as described in said reference. Such apparatus can also be advantageously combined with the infusion device of the present invention and is therefore incorporated herein by reference. This applies in particular to the structure of the valve device but also to the pump of said apparatus. However, WO 2004/012806 A1 is silent about the problem of fibrosis and thrombosis forming and building-up on the drug delivery exit port.

SUMMARY OF THE INVENTION

The object of the present invention therefore is to provide an implantable infusion device which may stay at the implantation site for long term use.

The infusion device according to the invention comprises an infusion needle and a drive unit coupled to the infusion needle and arranged for advancing the tip end of the infusion needle to penetrate any fibrosis when the device is implanted in the patient's body. At least the infusion needle and the drive unit are designed for implantation in the patient's body. Other components such as an energy source, a control unit, a data processing device and/or even a reservoir and/or pump for the drug may be extracorporal to complete the drug delivery system. However, it is preferred that the aforementioned components be implanted as well and, therefore, belong to the implantable infusion device, most preferably forming an integral part with the remaining components of the implantable infusion device so as to be implantable as a unitary piece.

The infusion device according to the present invention may rest at the implantation site over a long time either for single use or for multiple use. For instance, where it is likely that a patient will suffer an allergic attack, such as heavy allergic reactions affecting e.g. the respiratory tract, in the near future or possibly only within a year or two, the infusion device may be implanted in the patient's body for single use at the appropriate time. Over time, fibrosis will grow on the infusion device. However, at the time of use, the infusion needle may be advanced by the drive unit so as to penetrate any fibrosis, thereby allowing immediate drug delivery through the tip end of the infusion needle into the patient's body. Where the infusion device is implanted adjacent a blood vessel, the tip end of the infusion needle may be advanced into the blood vessel without any risk of formation of thrombosis prior to use.

Where the infusion device is implanted for multiple use, the drive unit is preferably configured for advancing and retracting the tip end of the infusion needle. Thus, each time when the drug is delivered to the patient, the infusion needle will be advanced, the drug injected and the infusion needle retracted again.

Preferably, the infusion needle is disposed within a body of the infusion device with the tip end of the infusion needle being arranged for passing through an outer wall of the body. This prevents any fibrosis from growing into the infusion needle, in which case the infusion needle would still be blocked even after penetrating any fibrosis that has built up in front of the needle.

While it is imaginable that the outer wall be opened for allowing the infusion needle to pass therethrough, it is preferred to arrange the needle for penetrating the outer wall. For that purpose, the outer wall may be made at least partly from a self-sealing material in respect of penetrations resulting from the infusion needle. While the entire body may be made from the self-sealing material, it is advantageous for stability reasons if the self-sealing material forms at least one window area in the outer wall, the window area being positioned for penetration by the tip end of the infusion needle. The window area may be formed by a self-sealing penetration membrane which is preferably integrated in the outer wall by press fitting it into the outer wall.

Typically, the self-sealing material would be made from a polymer material which preferably comprises silicon. Other biocompatible polymer materials may be employed as well.

The self-sealing material may also be a composite material. A particularly preferred embodiment of such composite material comprises at least one outer shape-giving layer and a self-sealing soft material contained within the outer layer. Thus, the outer layer forms a shell for the soft material. The outer layer may be made from a biocompatible polymer, such as one of those polymers mentioned above, and the self-sealing soft material may be a gel.

While the drive unit of the infusion device may be separate from the body housing the infusion needle, it is preferred to also dispose the drive unit entirely within the body of the infusion device so that the two components can be implanted as a single module.

According to one particularly preferred aspect of the present invention, the tip end of the infusion needle is laterally movable so as to vary the injection site. For instance, when the infusion device is implanted in a patient's body, it may be placed adjacent a blood vessel after free-dissecting the blood vessel. As set out above, frequent penetration of the same portion of the blood vessel would cause irritation and after a while penetration would become difficult or even impossible. Alternatively letting the infusion needle rest in place within the blood vessel would cause thrombophlebitis followed by thrombosis. Variation of the injection site by laterally displacing the needle at appropriate times may overcome such problems.

For this purpose, the drive unit may comprise a moveable carriage on which the infusion needle is mounted for lateral displacement of the tip end of the infusion needle. The movable carriage may e. g. comprise a turntable and/or a shuttle bus, such as in the form of a slide.

Preferably, the drive unit is configured so as to laterally displace the tip end of the infusion needle each time when said tip end is advanced and/or retracted.

Thus, lateral displacement and advancement/retraction of the tip end of the infusion needle are coordinated. The lateral displacement of the tip end of the infusion needle may take place before and/or after an injection. The mechanism may be such that after a certain number of lateral displacements or after lateral displacement over a predefined distance, the tip end of the infusion needle is laterally returned to its initial position so that the next number of infusions will take place again at locations that have previously been penetrated by the needle. This is particularly suitable where the tip end of the infusion needle is positioned for the penetration of a limited window area or where the infusion device is implanted adjacent a blood vessel.

The infusion needle of the infusion device preferably has a tube-like body closed at the tip end and having a laterally arranged delivery exit port for the delivery of drugs into the patient's body. Therefore, the needle will not cut out any material but will simply divide it during penetration. Thus, when the needle penetrates any material, such as fibrosis and/or the self-sealing penetration membrane, there will be no material entering and blocking the drug delivery passageway.

A reservoir is provided to be coupled to the infusion needle. Typically an infusion liquid will be contained in the reservoir. The reservoir may be arranged separate from the body of the implantable infusion device either for remote implantation within the patient's body or outside the patient's body. In the latter case, the external reservoir may be connected to the implanted infusion device via a stationary conduit. Refilling an external reservoir is generally easier than refilling an implanted reservoir and, therefore, this is advantageous where a substantial amount of drugs will have to be administered to the patient.

At least a section of a periphery of the reservoir may be made from a flexible material permitting volume changes of the reservoir by deformation of the flexible material as infusion liquid is filled into or drawn out of the reservoir. Thus, the reservoir may be of balloon type. The flexible material may comprise a polymer membrane. A bellow construction is preferable having pre-bent crises to reduce long term degradation.

According to a particular embodiment, drawing liquid from the reservoir may cause a pressure decrease in at least part of the reservoir so that a negative pressure is attained as compared to the pressure in front of the infusion needle. For instance, the reservoir may comprise a gas chamber and a liquid chamber, said chambers being separated by a membrane, e. g. the polymer membrane. When liquid is drawn from the liquid chamber, the pressure in the gas chamber will decrease accordingly.

The reservoir may have an injection port for injecting liquid from outside the human body into the implanted reservoir. That way, the reservoir implanted in the patient's body along with the infusion device may be kept small since the reservoir can be refilled easily at appropriate time intervals.

Preferably, the injection port comprises a self-sealing material in respect of penetrations caused by a replenishing syringe that would be typically used to refill the reservoir through the patient's skin. It is preferable to implant the infusion device, or at least the self-sealing injection port of the reservoir, subcutaneously in the patient's body so that it is easily accessible for refill by means of the syringe.

Where the reservoir forms part of the body of the infusion device, at least a section of a periphery of the reservoir, such as the self-sealing injection port and/or the volume change permitting flexible material, may at least partially constitute the outer wall of the body of the infusion device.

While the reservoir may be compressed automatically or preferably manually in order to inject drugs through the needle into the patient's body, it is preferred to couple a pump between the reservoir and the infusion needle for pumping the drugs from the reservoir to the infusion needle. By means of the pump, it is easy to measure out an exact dose of the drug.

While the type of pump is not critical in the case of extracorporal use thereof in connection with an external reservoir, one specific type of pump is particularly preferred when the pump is implanted along with the implantable infusion device. More particularly, an implantable pump preferably comprises a valve device having a first and a second valve member, each of the said first and second valve members having a smooth service facing each other so as to form a sealing contact between the first and second valve members and further having different liquid channels that can be brought into alignment by displacement of the two smooth surfaces relative to one another while maintaining the sealing contact. This type of pump is described in great detail in WO 2004/012806 A1 referred to above. The first and second valve members are preferably made from a ceramic material for its excellent sealing capabilities over a long period of time and its inertness to many substances.

The pump may be a membrane type pump, as also described in WO 2004/012806 A1, but is not restricted to this type of pump. The membrane type pump may comprise a membrane displaceable by a piston as the piston moves, the piston being coupled to the valve device so as to slidably displace the first and second valve members relative to one another as the piston moves. Where the infusion needle is disposed within a body of the infusion device, the pump may also be contained in the body of the infusion device or it may be separate from the body of the infusion device for remote implantation within the patient's body.

The pump and/or the drive unit for advancement, retraction and possibly for lateral displacement of the tip end of the infusion needle may be actuated manually. This is particularly practical where the pump is provided extracorporally separate from the implanted infusion device. Where the pump is implanted along with the infusion device, it may be actuated by mechanical remote control or, more preferably, by a pressure sensitive switch arranged so as to be manually operable when implanted subcutaneously in the patient's body.

Preferably, manual actuation of either the pump or the drive unit simultaneously causes actuation of the other, i.e. the drive unit or the pump. For instance, the pressure built up by the pump may cause the drive unit to advance the infusion needle and when the infusion liquid has been delivered through the tip end of the needle into the patient's body, the pressure relief in the pump will allow a return spring or other resilient means to retract the infusion needle. A mechanical stepper may cause the infusion needle to be laterally displaced upon each advancement and/or retraction.

Instead of manual actuation of the pump and/or drive unit, at least one motor may be provided. The motor may be arranged e. g. for electrically, magnetically or electromagnetically actuating the pump and/or drive unit or for hydraulically actuating the pump and/or drive unit. Preferably, the motor is arranged for actuating either the pump or the drive unit, thereby causing simultaneous actuation of the other, i.e. the drive unit or the pump. A motor may also be provided for actuation of any other energy consuming part of the infusion device.

The term "motor" in the sense of the present invention includes anything that employs energy other than manual power and either automatically transforms such energy into kinetic or hydraulic or another type of energy or directly uses such energy to activate the pump, drive unit and/or other part of the infusion device and drug delivery system. As such, it is possible that part of the drive unit also forms a part of the motor, e.g. in the case of an electromagnetically actuated drive unit.

Where the motor forms part of the infusion device and, therefore, is implanted within the patient's body along with the infusion device either separate from the body of the infusion device for remote implantation within the patient's body or contained in the body of the infusion device, coupling elements may be provided either for conductive or for wireless energy transfer from outside the device to the motor. For instance, the motor may be arranged for being wirelessly driven by an external electromagnetic field.

An external energy source for use outside the patient's body, such as a primary energy source or a battery, in particular a rechargeable battery, that may be mounted on the patient's skin may be used to provide energy to the pump and/or drive unit and/or any other energy consuming part of the infusion device. The energy source may in particular be connected to the at least one motor for actuating these components. An external energy source for wireless energy transfer may be adapted to create an external field, such as an electromagnetic field, magnetic field or electrical field, or create a wave signal, such as an electromagnetic wave or sound wave signal.

Where the energy is wirelessly transferred to the implanted infusion device, a transforming device for transforming the wirelessly transferred energy into electric energy may be provided. Such transforming device is preferably adapted to be placed directly under the patient's skin so as to minimize the distance and the amount of tissue between the transforming device and the energy supply means outside the patient's body.

An energy transmission device for wireless energy transfer from the energy source and/or energy storage means to the transforming device may be adapted to generate an electromagnetic field. Alternatively or in addition, the energy transmission device for wireless energy transfer may be adapted to generate a magnetic field. Also, the energy transmission device for wireless energy transfer may be adapted to generate an electrical field. The wireless energy may also be transmitted by the energy transmission device by at least one wave signal. Such signal may comprise an electromagnetic wave signal, including at least one of an infrared light signal, a visible light signal, an ultraviolet light signal, a laser signal, a microwave signal, a radio wave signal, an X-ray radiation signal and a y-radiation signal. Also, the wave signal may comprise a sound or ultrasound wave signal. Furthermore, the wireless energy may be transmitted as a digital or analog signal or a combination thereof.

Instead of or in addition to an external energy source, the implantable infusion device may itself be provided with an energy source. Such energy source may be part of or may be contained within the body of the infusion device. However, it may also be provided separate from the body of the infusion device for remote implantation within the patient's body.

Such implantable energy source preferably comprises energy storage means, such as a long-life battery or, more preferably, an accumulator. The accumulator has the advantage of being rechargeable. Preferably, the accumulator comprises a rechargeable battery and/or a capacitor.

Again, coupling elements for conductive or wireless energy transfer from a primary energy source outside the device to the accumulator may be provided for charging the accumulator from outside the patient's body when the device is implanted in the patient's body. Similarly, the accumulator may comprise coupling elements for conductive and/or wireless energy supply to the at least one motor of the infusion device.

While the at least one motor may be provided with actuating means for manual activation of the motor, it is preferred to provide a control unit for controlling the at least one motor. The control unit may also be used to control the pump, drive unit and/or any other energy consuming part of the infusion device and, where the device includes an internal or external energy source, may even be used to control such energy source. The control unit may be adjusted to the patient's individual needs, such that the appropriate amount of medicine will be administered at appropriate time intervals. Automatic administration will substantially relieve the patient.

Preferably, the control unit has a data transfer port for data transfer between an external data processing device outside the patient's body and the control unit implanted in the patient's body, regardless of whether the control unit is contained in the body of the infusion device or whether it is implanted within the patient's body remote from the body of the infusion device. Said data transfer port allows for supervising the control unit to adapt the infusion device to changing needs of the patient. Preferably, the data transfer port is a wireless transfer port for the data transfer, so as to provide easy data exchange between the control unit and the data processing device, e. g. during a visit at the doctor's. Most preferably, the control unit is programmable to further increase its adaptation flexibility.

The control unit—with or without the data transfer port—may also be provided extracorporally, e. g. mounted on the patient's skin. An external control unit has the advantage of being easily accessible in case of any failure. It is preferably adapted for wireless remote control of the at least one motor implanted with the infusion device.

A control signal transmission device may be provided for wireless transmission of an extracorporal control signal to an implanted motor. Similarly, a data transmission interface for wirelessly transmitting data from outside the patient's body to a control unit implanted inside the patient's body may be provided. Again, the wireless control signal and/or data transmission may comprise one of the aforementioned wave signals, being digital or analog or a combination thereof. More preferably, the control signal may be transmitted in the same manner as the energy is transmitted to the motor. For instance, the control signal may be transmitted by modulation of the energy signal, the energy signal thereby serving as a carrier wave signal for the digital or analog control signal. More particularly, the control signal may be a frequency, phase and/or amplitude modulated signal.

Apart from or as a part of the control unit, feedback may be provided on parameters relevant for the treatment of the patient. Such parameters may be either physical parameters of the patient and/or process parameters of the device. For that purpose, at least one feedback sensor is provided for detecting such parameters. For instance, the feedback sensor may be adapted to detect one or more parameters related to any of the following: kind of blood cells, drug level, glucose level, oxygen level, ph level, flow volume in blood vessel, pressure, electrical parameters, distension, distance etc.

The feedback sensors may be connected to the control unit and the control unit may comprise a control program for controlling drug delivery in response to one or more signals of the feedback sensors. In addition or alternatively, feedback data may be transferred from the control unit to the external data processing device. Such feedback data may be useful for the doctor's diagnosis.

The infusion device, as discussed above, may be implanted in the patient's body at various locations. For instance, implantation of the infusion device—or a part thereof—in the patient's abdomen or thorax might be the proper choice where the infusion device or, e. g., its reservoir is relatively voluminous. In that case, one might argue that it may be preferable to implant the infusion device with a completely filled reservoir as it might be difficult to refill the reservoir in the abdomen. However, a subcutaneously positioned injection port connected via a tube to the reservoir may be suitable in this case.

Alternatively, as discussed above, the infusion device may be implanted subcutaneously. Subcutaneous implantation increases the possibilities of wireless energy and/or data transfer between the infusion device and an extracorporal component of the drug delivery system. Also, refilling the reservoir through an injection port by means of a replenishing needle penetrating through the patient's skin is substantially facilitated when the infusion device is implanted subcutaneously. By means of the replenishing needle, the reservoir may be filled with a volume of infusion liquid of a predetermined dose. It should be understood, however, that depending upon the circumstances any part of the infusion device may be placed in the abdomen or thorax and other parts subcutaneously.

Depending on the individual treatment, it may be advantageous to implant the infusion device within fat tissue or intramuscularly or adjacent a blood vessel or the gastrointestinal or urinary tract, such as the patient's kidneys, so that the infusion liquid will be injected into the tissue, the muscles or directly into the blood vessel, gastro-intestinal tract or urinary tract. The advantages that may be obtained by a proper choice of location of the infusion device are various and may include better resorption of the drugs when delivered directly so that the drugs will act more quickly and/or may be delivered at a higher dose.

The various aforementioned features of the invention may be combined in any way if such combination is not clearly contradictive. The invention will now be described in more detail in respect of preferred embodiments and in reference to the accompanying drawings. Again, individual features of the various embodiments may be combined or exchanged unless such combination or exchange is clearly contradictive to the overall function of the device.

DETAILED DESCRIPTION OF THE DRAWINGS

Figure 1:
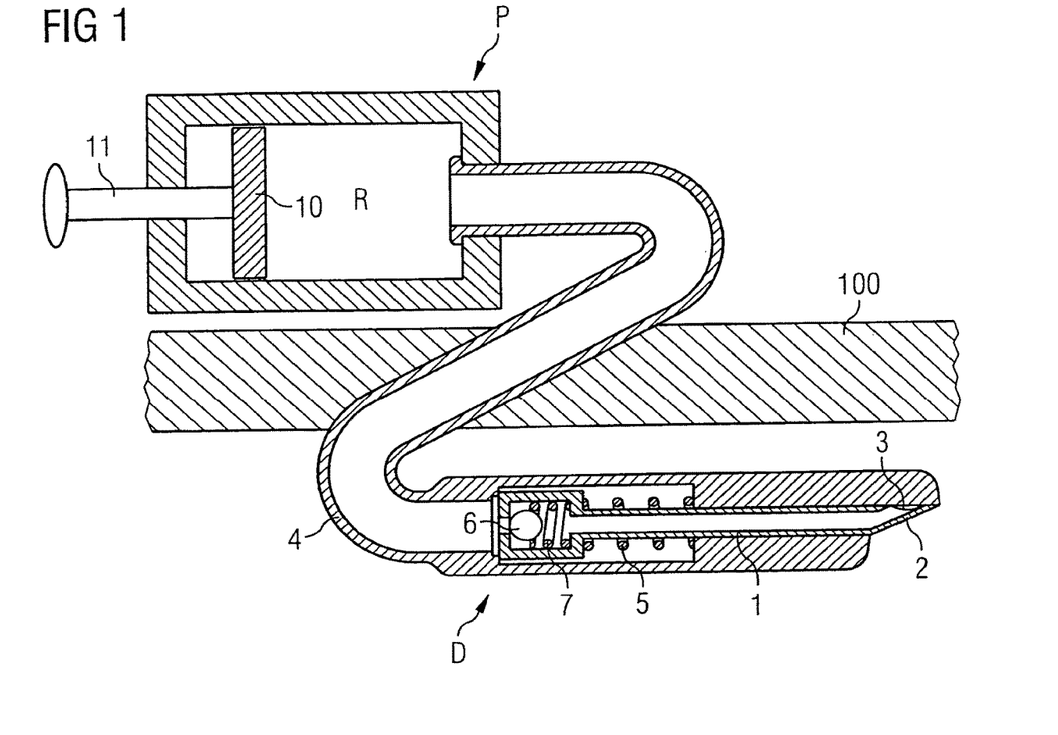
FIG. 1 shows a strictly mechanical infusion device according to a first embodiment of the invention.

FIG. 1 shows a strictly mechanical, more exactly a hydro-mechanical, infusion device implanted subcutaneously under a patient's skin 100. The infusion device comprises a needle 1 having a tip end 2. Tip end 2 is closed at its distal end and has a lateral drug delivery exit port 3. Needle 1 is arranged for longitudinal displacement within an open-ended tube 4 upon activation by a drive unit D.

Tube 4 penetrates the skin 100 and is attached to an extracorporal pump P. Pump P is schematically shown and can be designed in many ways. In the embodiment shown in FIG. 1, reservoir R with infusion liquid to be delivered to the patient is part of pump P. Alternatively, reservoir R could be separate from pump P and connected thereto, e.g. as principally shown in FIG. 2. In the embodiment of FIG. 1, however, a piston 10 of pump P is manually displaceable by means of an actuator 11 in the form of a piston rod so as to pump the infusion liquid from reservoir R through tube 4 towards needle 1. Instead of being manually driven, the pump could be motor-driven, and the motor could be automatically controlled so as to deliver a certain amount of drugs at certain time intervals. Reservoir R, pump P and/or other components of the drug delivery system, such as the aforementioned motor, automatic control for the motor, etc., may alternatively be implanted along with infusion needle 1 and drive unit D. Other modifications are possible and will become apparent upon further consideration of the embodiments described later in reference to FIGS. 2 to 8.

In the infusion device shown in FIG. 1, as the pressure is increased in reservoir R by actuation of piston 10, this will result in a displacement of needle 1 against the force of a spring 5 of drive unit D. Thus, tip end 2 of needle 1 will penetrate any fibrosis having built up in front of the infusion device. When return spring 5 is completely compressed and the pressure exerted on the infusion liquid by means of piston 10 is further increased, a ball valve 6 will be displaced against a second return spring 7 which is stronger than the first return spring 5. That way, as long as the pressure is held at a sufficiently high level, infusion liquid will be pumped from reservoir R through tube 4, hollow needle 1 and the needle's exit port 3 into the patient's body. Upon pressure release, ball valve 6 will close due to return springs 5 and 7, and then needle 1 will be retracted to its initial position shown in FIG. 1.

The fit between the outer surface of needle 1 and the inner surface of tube 4 should be sufficiently tight to prevent any fibrosis from growing in.

It should be noted that the force acting on needle 1 to advance the same may be calculated as the product of the actual pressure and the cross section of needle 1. Since the cross section of a typical infusion needle is relatively small, high pressure will have to be exerted in order to penetrate any fibrosis and to overcome the counteracting forces of return springs 5 and 7. It is therefore advantageous to construct drive unit D such that two strictly separated chambers are formed in front of and behind the drive unit. Thus, when the chamber behind drive unit D is kept at low pressure, such as ambient pressure, the force acting on needle 1 would correspond to the product of the actual pressure and the entire cross section of drive unit D and, thus, be substantially higher.

Figure 2:
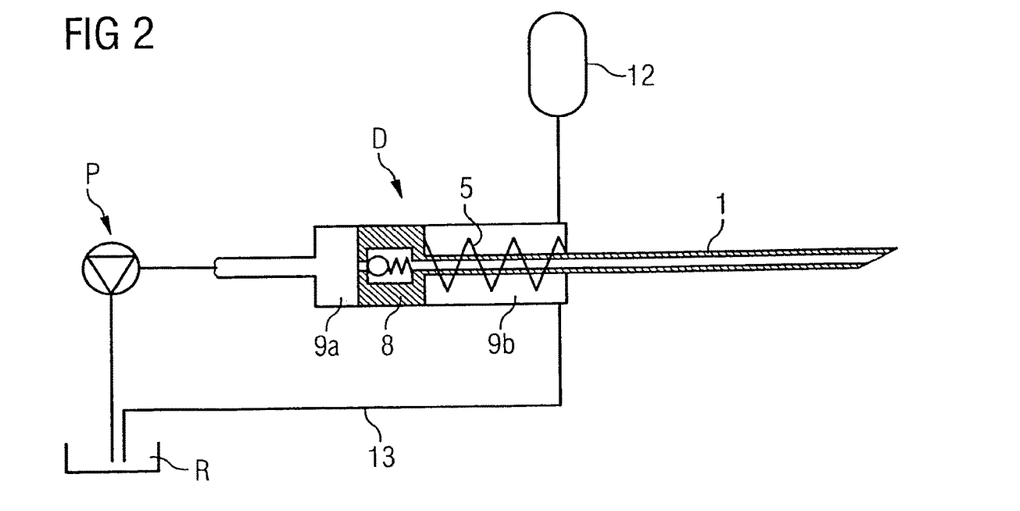
FIG. 2 shows the infusion device of FIG. 1 diagrammatically with some modifications.

This is shown in FIG. 2. Drive unit D comprises a piston 8 to which needle 1 is attached as shown in FIG. 1. Piston 8 separates a first chamber 9a in front of piston 8 and a second chamber 9b behind piston 8. While the pressure in first chamber 9a corresponds to the pressure exerted by pump P, the pressure in second chamber 9b can be kept at a lower value.

For instance, chamber 9b could be filled with a compressible gas. In that case, return spring 5 could be dispensed with as the compressed air would already create a needle retraction force.

It is, however, difficult to securely seal a gas chamber. Therefore, second chamber 9b is instead filled with liquid, such as the infusion liquid, and the liquid may be urged into a flexible volume 12. The flexible volume 12 could be of simple balloon type so as to fill up without exerting any strong counter force. Alternatively, the flexible volume 12 may comprise a gas chamber separated from the liquid of second chamber 9b by a flexible membrane. Again, return spring 5 could be dispensed with in this case.

Instead of the flexible volume 12, a conduit 13 may connect second chamber 9b with reservoir R. Thus, when needle 1 is advanced, liquid will be dispelled from second chamber 9b through conduit 13 into reservoir R, and as needle 1 is retracted by means of return spring 5, liquid will be drawn from reservoir R through conduit 13 back into second chamber 9b.

Clearly, pump P and reservoir R may be implanted into the patient's body along with drive unit D and needle 1, either remote thereof or as a single unit, if desired.

Figure 3:
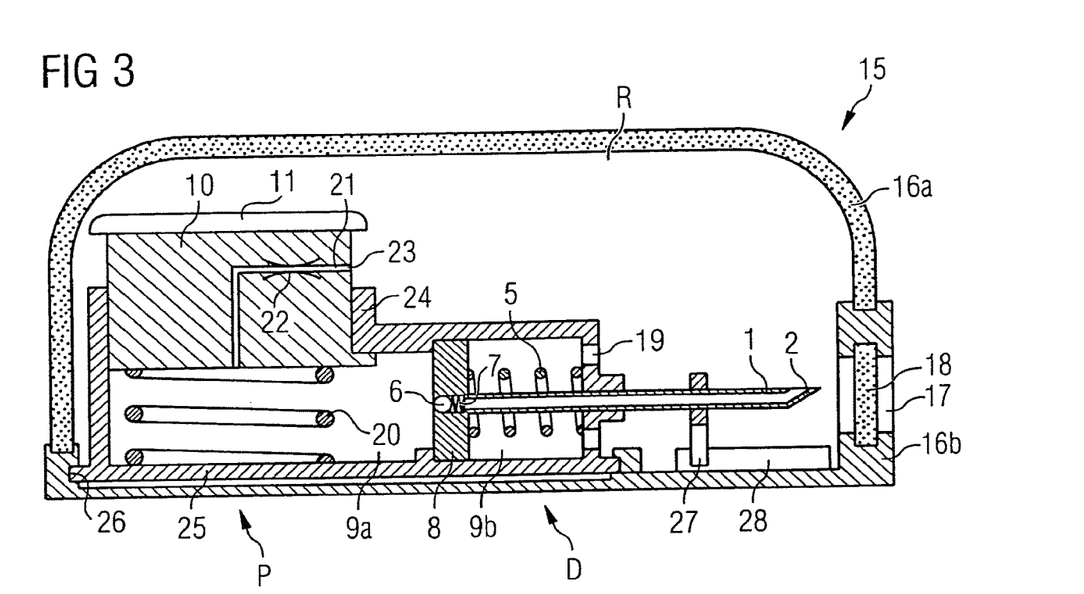
FIG. 3 shows a cross sectional view of a strictly mechanical, completely implantable infusion device according to a second embodiment of the invention.

FIG. 3 shows a completely implantable, strictly mechanical infusion device to be implanted subcutaneously. The individual components of the device are contained within a unitary body 15 comprising an outer wall 16a, 16b. The volume defined by outer wall 16a, 16b is completely filled with infusion liquid. A wall portion 16a is flexible so as to allow for volume changes occurring with each injection and refill. Wall portion 16a is made from a polymer material which is self-sealing with respect to the penetration of a replenishing needle. The infusion device can thus be refilled with infusion liquid through the polymer wall portion 16a while being implanted subcutaneously.

The other wall portion 16b is rigid to provide some stability for the individual components contained within body 15. A window area 17 is formed in rigid wall portion 16b and a penetration membrane 18 is sealingly press fitted in window area 17. Penetration membrane 18 is made from a self-sealing material in respect of penetrations resulting from infusion needle 1, which infusion needle is arranged for penetrating window area 17.

Needle 1 is connected to a piston 8 separating a first chamber 9a in front of piston 8 and a second chamber 9b behind piston 8, as discussed above in reference to FIG. 2. A return spring 5 and a ball valve 6 with a return spring 7 are also provided. Openings 19 are provided to connect second chamber 9b to reservoir R so that when the pressure is raised in first chamber 9a piston 8 may dispel infusion liquid from second chamber 9b through openings 19 into reservoir R, which reservoir R is approximately at ambient pressure.

The pressure in first chamber 9a is increased by means of a pump P comprising a piston 10 formed as a unitary piece with an actuator 11 in the form of a manually actuated push button. A return spring 20 serves to urge piston 10 into its initial position shown in FIG. 3. A flow passage 21 is formed in the piston 10 with a flow constriction 22 and an exit opening 23 arranged a short distance above a housing 24 in which piston 10 is slidably arranged.

The infusion device shown in FIG. 3 functions as follows. When arranged subcutaneously with the push button 11 facing the skin, the patient may press down the push button 11 against the spring force of return spring 20. Due to flow constriction 22 in flow passage 21, the infusion liquid contained in first chamber 9a will not flow back into reservoir R through flow passage 21 but will urge piston 8 with needle 1 towards window area 17 while expelling infusion liquid from second chamber 9b through openings 19 into reservoir R. When piston 8 is in its end position and push button 11 is pressed down further, the pressure in first chamber 9a will eventually rise to a level sufficiently high to overcome the spring force of return spring 7, thereby opening ball valve 6 and allowing infusion liquid to be discharged through hollow needle 1, the tip end 2 of which has meanwhile penetrated penetration membrane 18 and any fibrosis built up thereon. Upon pressure release, ball valve 6 will immediately close and return spring 20 will urge push button 11 back into its initial position while simultaneously drawing back piston 8 with infusion needle 1 into its retracted position. Return spring 5 could be dispensed with and merely serves as a safety means. The flow passage 21 is needed to allow push button 11 to move further up even after piston 8 has reached its starting position, thereby drawing additional infusion liquid from reservoir R into first chamber 9a, which additional infusion liquid compensates the amount of infusion liquid delivered to the patient during the injection cycle.

The infusion device shown in FIG. 3 provides several advantages such as being strictly mechanical, not involving any gas chambers and not requiring any particular sealing of the piston elements 8 and 10.

In addition to the advancing and retracting capabilities of drive unit D, the drive unit of the infusion device shown in FIG. 3 further comprises means for laterally displacing the tip end of the infusion needle 1. In the particular embodiment of FIG. 3, a specific example of such lateral displacing means is shown. More particularly, needle 1 is mounted on a turntable 25 which is rotatably mounted in a circular groove 26 of second wall portion 16b. Furthermore, a guide pin 27 is securely mounted on the needle 1 to cooperate with a guide structure 28 securely fixed to rigid wall portion 16b of outer wall 15. Upon advancement or retraction of infusion needle 1, guide pin 27 will be guided in guide structure 28 and thereby laterally displace infusion needle 1, which lateral displacement causes rotation of turntable 25 within circular groove 26.

Figure 4:
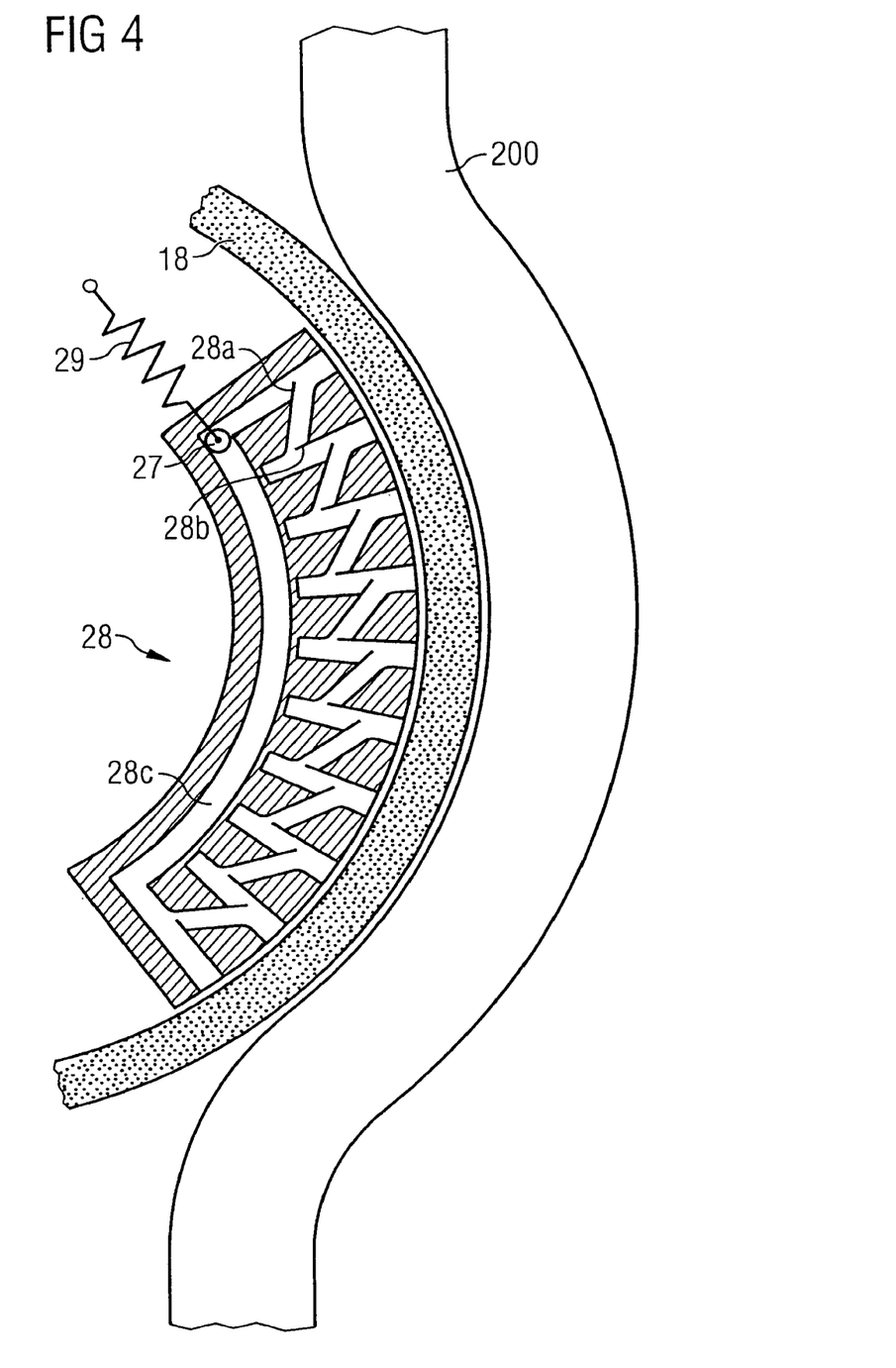
FIG. 4 shows a plan view of a part of the infusion device of FIG. 3, located adjacent a blood vessel.

The principle of guide structure 28 will now be described in more detail in relation to FIG. 4. Resilient flaps 28a, 28b within guide structure 28 serve to guide guide pin 27 through the entire guide structure 28 upon repeated advancement and retraction of infusion needle 1. Guide structure 28 is designed to provide ten different injection sites through penetration membrane 18 into a blood vessel 200 located adjacent penetration membrane 18. Where it is desired, the trajectory of guide structure 28 may include a return path 28c for guide pin 27 to return to its starting position shown in FIG. 4. Such return action will be caused by a return spring 29 fixed to the rigid second wall portion 16b.

It should be noted that all components of the infusion device shown in FIG. 3 may be made from polymer material although it is preferable that at least infusion needle 1 and return springs 5, 7, 20, 29 be made from an inert metal.

Figure 5:
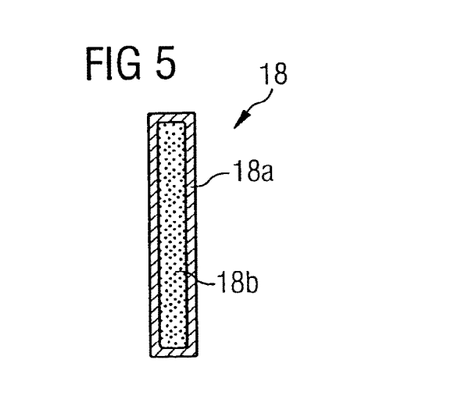
FIG. 5 shows a cross sectional view of a penetration membrane made from a composite material.

FIG. 5 shows a preferred embodiment of penetration membrane 17 in the form of a composite material. The same material can also be used for the flexible first wall portion 16a of outer body 15 or for an infusion port that will be described below in connection with another embodiment of the invention. The composite material of penetration membrane 17 shown in FIG. 5 comprises an outer shape-giving layer 17a defining a volume in which a self-sealing soft material 17b is contained. Self-sealing soft material 17b can be of gel type having a viscosity such that it does not flow through any penetrations caused by infusion needle 1 during penetration of outer shape-giving layer 17a. Instead of a single outer shape-giving layer 17a, shape-giving layer 17a may comprise a plurality of layers. Outer shape-giving layer 17a preferably comprises silicon and/or polyurethane, since such materials can be produced to have self-sealing properties in respect of penetrations resulting from infusion needle 1.

Figure 6:
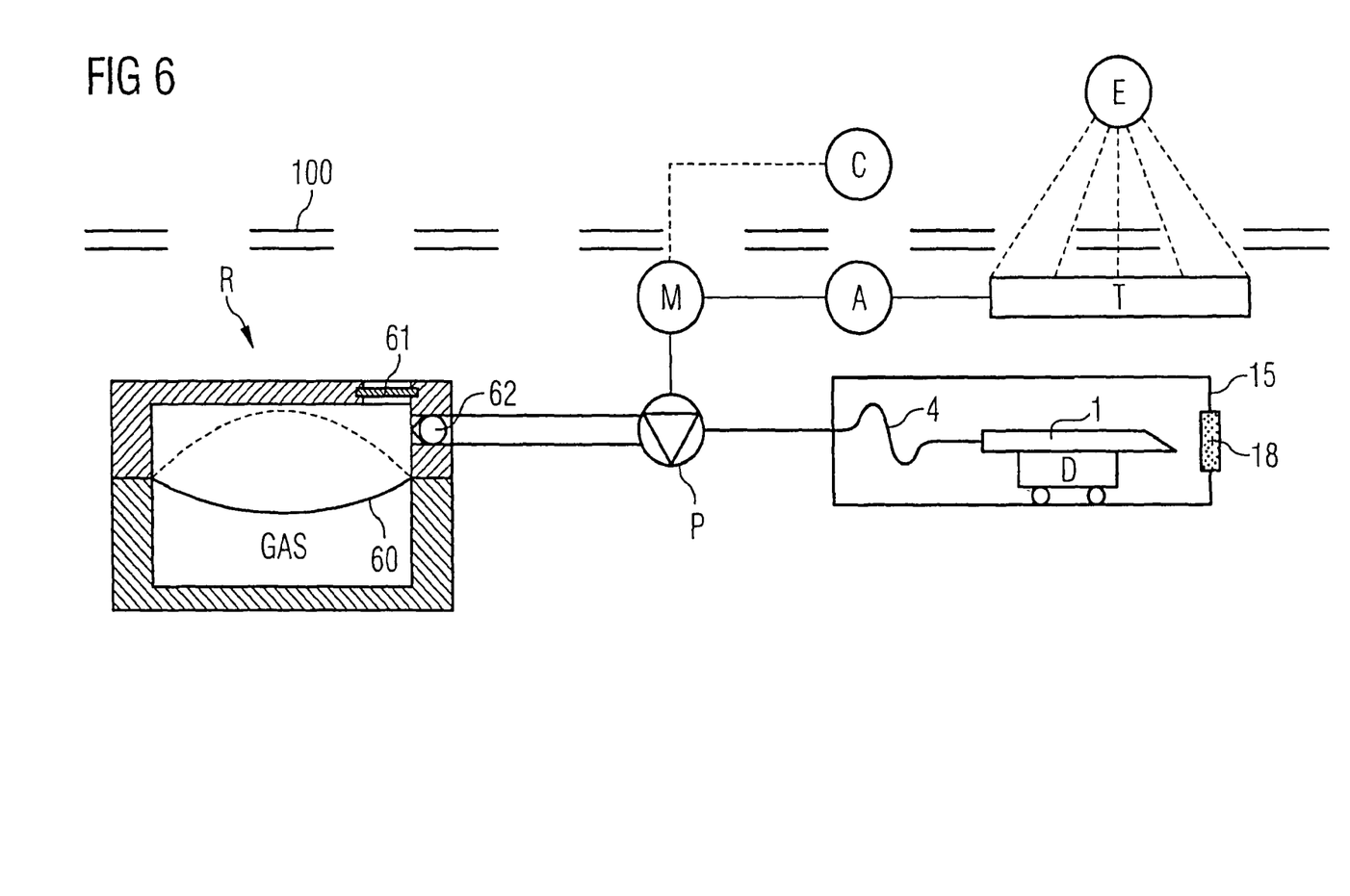
FIG. 6 shows a motor-driven infusion device according to a third embodiment of the invention.

FIG. 6 shows a fully automatic embodiment of the infusion device according to the present invention. It is to be understood, however, that manually operated elements as discussed above and automatically operating elements as discussed herein below may be combined and interchanged where this is possible. The overall drug delivery system in FIG. 6 is shown schematically, wherein all components disposed underneath the patient's skin 100 are part of the implantable infusion device whereas the components above the patient's skin 100 are needed to complete the drug delivery system.

A pump P driven by a motor M connects a reservoir R with an infusion needle 1 mounted on a drive unit D within a body 15 so as to penetrate upon advancement a penetration membrane 17 of body 15. A fluid conduit 4 is long enough to compensate for the advancement of infusion needle 1. While drive unit D may be activated hydraulically by forces generated by pump P, similar to the embodiments discussed above, a separate motor may be provided to actuate drive unit D. Alternatively, motor M may be designed to actuate drive unit D and any movement of drive unit D may cause pump P to pump.

Although the embodiment shown in FIG. 6 may comprise one of a great variety of reservoir types, a particular reservoir type will now be described. The volume of reservoir R shown in FIG. 6 is divided into two sections by means of a membrane 60. One section is filled with gas whereas the other section is filled with infusion liquid. An infusion port 61 allows for refilling reservoir R with infusion liquid by means of a replenishing needle. When reservoir R is in its full state, the gas section is at ambient pressure or over-pressurized. As infusion liquid is drawn from reservoir R upon each infusion cycle, the pressure in the gas section will decrease below ambient pressure, i.e. to a negative relative value. Depending upon the particular type of pump P, it may be advantageous to provide a single acting ball valve 62 to prevent any back flow from pump P to reservoir R.

Motor M is wirelessly controlled by a control unit C from outside the patient's body. Control unit C determines the time period between infusion cycles as well as the amount of infusion liquid to be injected into the patient's body upon each infusion cycle. Instead of wireless communication between control unit C and motor M, galvanic contacts may be provided through the skin 100. Also, the control unit C may be implanted along with motor M. In that case, control unit C is preferably programmable from outside the patient's body, either wirelessly or through galvanic contacts, so as to allow proper configuration of the control unit according to changing demands.

In addition to or instead of control unit C, a pressure sensitive switch for activating motor M may be arranged subcutaneously.

There are various ways of providing motor M with energy. For instance, energy may be supplied from outside the patient's body either for direct use by motor M and/or for charging an accumulator A, such as a rechargeable battery and/or a capacitor. In the embodiment shown in FIG. 6, an extracorporal primary energy source E transmits energy of a first form through the patient's skin 100 to an energy transforming device T which transforms the energy of the first form into energy of a second form, such as electric energy. The electric energy is used to recharge accumulator A which provides secondary energy to motor M upon demand.

In general, external energy source E may be adapted to create an external field, such as an electromagnetic field, magnetic field or electrical field, or create a wave signal, such as an electromagnetic wave or sound wave signal. For instance, energy transforming device T as shown in FIG. 6 may act as a solar cell, but adapted to the particular type of wave signal of primary energy source E. Energy transforming device T may also be adapted to transform temperature changes into electrical energy.

Instead of an external primary energy source E, an implantable primary energy source E may be used, such as a regular long-life battery instead of accumulator A.

The energy signal can also be used to transmit control signal of the control unit C by appropriate modulation of the energy signal, regardless of whether the energy is transmitted wirelessly or by wire, the energy signal thereby serving as a carrier wave signal for the digital or analog control signal. More particularly, the control signal may be a frequency, phase and/or amplitude modulated signal.

Figure 7:
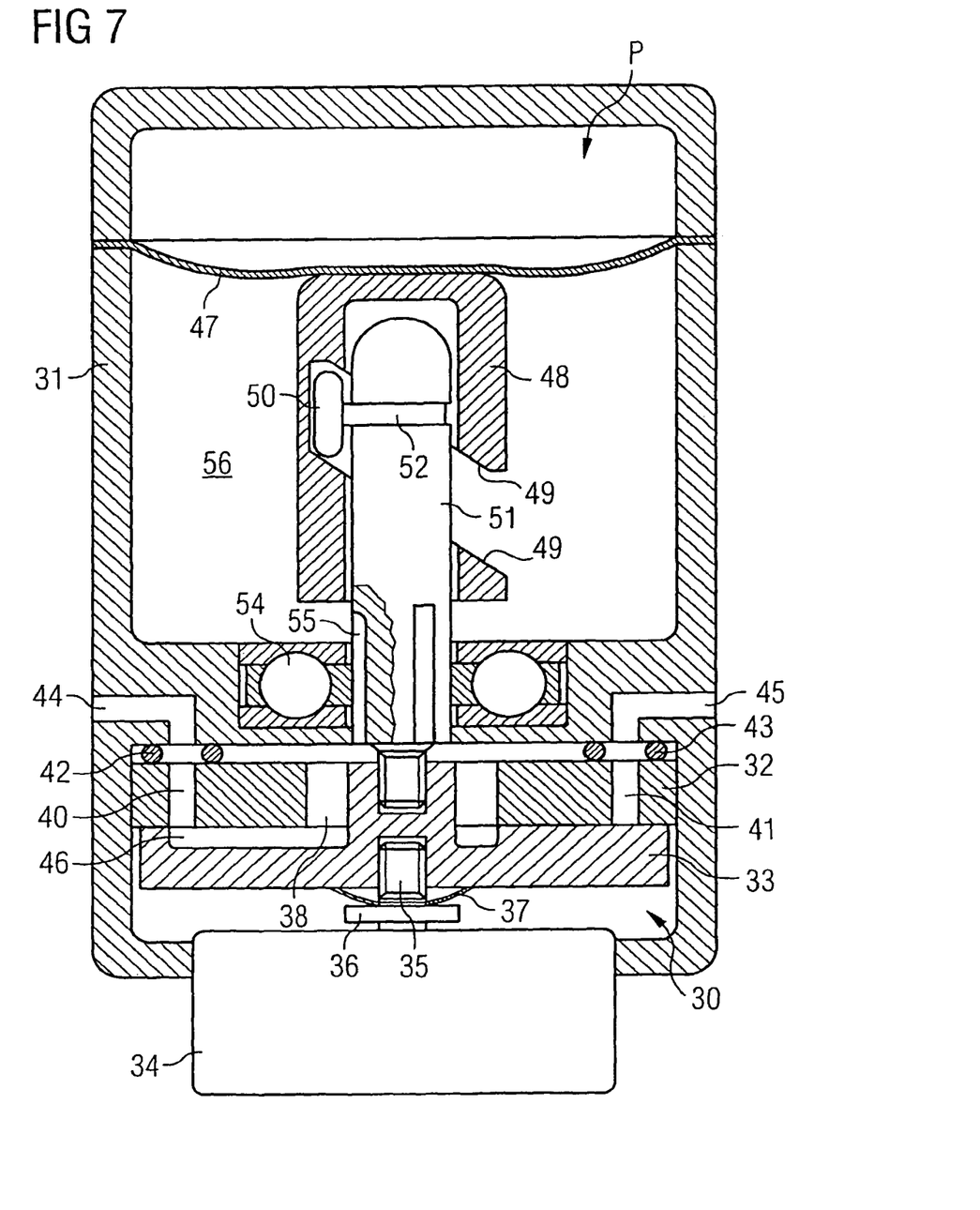
FIG. 7 shows a motor-driven pump unit suitable for use in connection with the embodiment shown in FIG. 6.

FIG. 7 shows a cross sectional view of a motor-pump unit that could be used in connection with the arrangement shown in FIG. 6. This motor-pump unit is extensively described in WO 2004/012806 A1 and the other pump units disclosed therein may be employed in connection with the present invention as well. The motor-pump unit comprises a valve pump assembly, wherein a membrane pump P and a valve pump device 30 constitute two main elements of the assembly mounted in a cylindrical housing 31. Valve device 30 includes a first valve member in the form of a ceramic disc 32 stationary mounted on and fixed to housing 31, and a second valve member in the form of a ceramic disc 33 facing and touching ceramic disc 32 and rotatable relative to stationary disc 32. A motor 34 is mounted on housing 31 enclosing ceramic discs 32 and 33. Motor 34 includes a splined motor shaft coupled to corresponding splines in an under central hole in rotatable disc 33 to allow disc 33 to move somewhat in an axial direction relative to motor shaft 35, although disc 33 follows the rotation of motor 31. On motor shaft 35 is mounted a stop member 36 and a spring washer 37 that exerts a slight amount of pressure against disc 33 to urge it against stationary disc 32.

Pump P includes a pump membrane 47 that can be any kind of membrane. Preferably, membrane 47 is a metal membrane, for example a titanium membrane, or a type of coated plastic material for achieving long lifetime and avoiding diffusion of liquid through membrane 47 over time. An operation device, which in this embodiment is incorporated in the valve pump assembly, includes a cam sleeve 48 which has a cut-out groove with two opposite cam surfaces 49, a cam wheel 50, which rotates in the cut-out groove pushing against cam surfaces 49, and a pump shaft 51 connected to rotary disc 33. Cam wheel 50 is mounted via a cam wheel shaft 52 onto pump shaft 51. Pump shaft 51 rotates because it is connected to rotating disc 33 via a splined shaft 57 that is coupled to corresponding splines in an upper central hole 53 in rotatable disc 33. The described spline coupling allows disc 33 to move somewhat in an axial direction relative to pump shaft 51. Pump shaft 51 is mounted in an encapsulated ball-bearing 54 and is stationary in an axial direction with respect to ball-bearing 54. Several elongated grooves 55 on pump shaft 51 extend past ball-bearing 54 and serve as liquid flow passages between first channel 38 of stationary disc 32 and a pump chamber 56 under membrane 47.

When motor 34 is rotating, membrane 47 moves up and down. As membrane 47 moves up and down, rotatable disc 33 connects first channel 38 alternately to second and third channels 40 and 41 so that liquid is either transmitted from second channel 40 or third channel 41 to pump chamber 56 or received from pump chamber 52 by second channel 40 or third channel 41, respectively. In FIG. 7, first channel 38 is shown as being connected to second channel via opened channel 46 so that second channel 40 receives liquid through first channel 38 from chamber 56.

The particular material selected for discs 32 and 33 is important because the selected material must be able to function using very fine tolerances without such discs sticking to one another over time. There are several materials available on the market that are suitable for this purpose, e. g. ceramic or ceramic mixed with other materials, such as carbon fiber.

Figure 8:
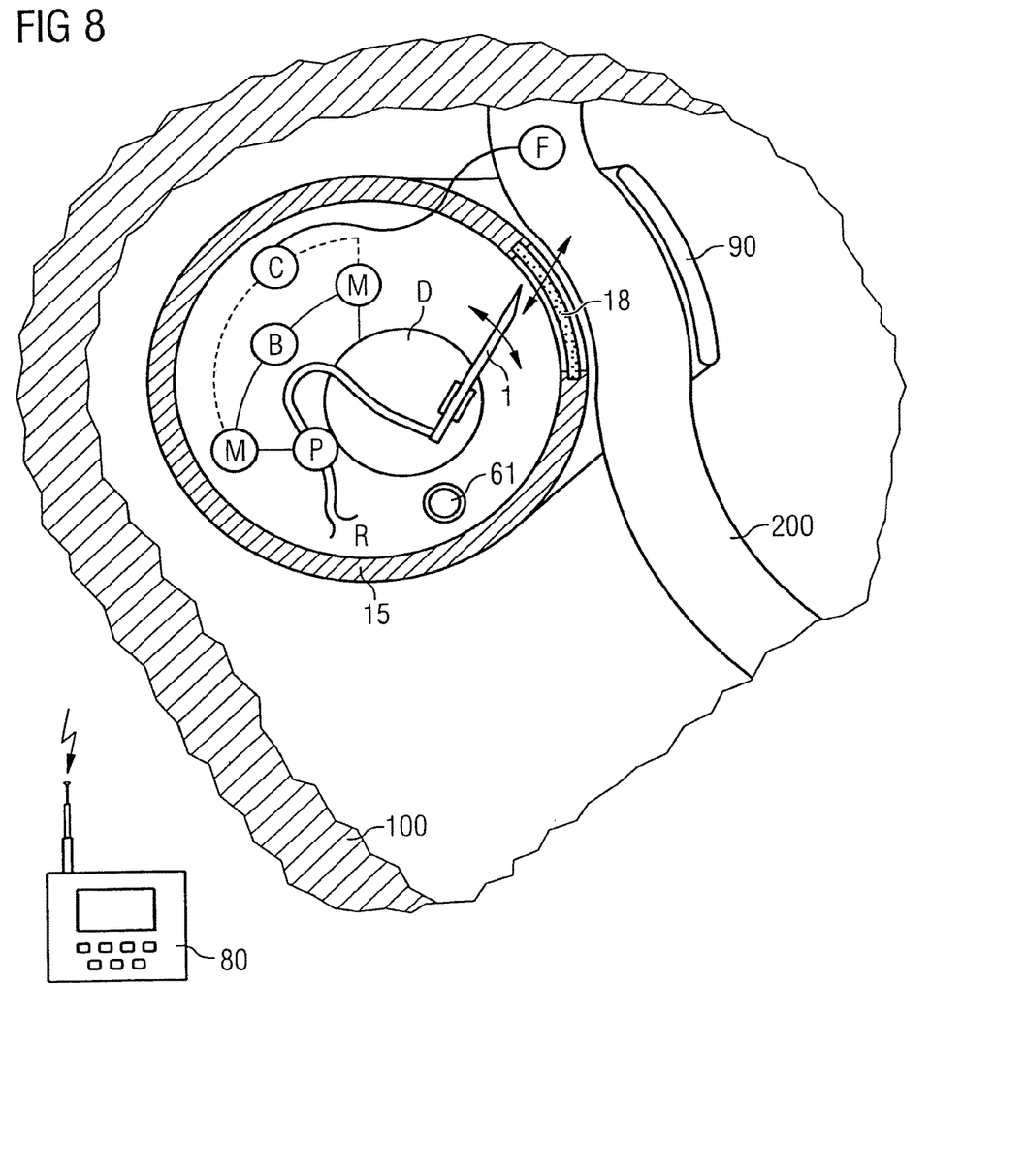
FIG. 8 shows a fully automatic unitary infusion device implanted subcutaneously adjacent a blood vessel.

FIG. 8 shows a third embodiment of the present invention with the infusion device being automatically driven and all components of the infusion device being contained within an outer body 15. The device is substantially disc-shaped with a lateral extension with a holder 90 for blood vessel 200 to maintain blood vessel 200 proximate the body 15. The infusion device shown in FIG. 8 is seen through a window in the patient's skin 100 while being implanted subcutaneously. Skin 100 covers the flat surface of the disc-shaped device.

Infusion needle 1 is mounted on a turntable which is part of drive unit D. Upon rotation of the turntable, the tip end of infusion needle 1 will move laterally along window 18 which is positioned proximate blood vessel 200. More particularly, infusion needle 1 is mounted on the turntable so as to be axially movable thereon back and forth such that its tip end will pass through window 18 at an inclined angle. Due to the inclination angle, the tip end of infusion needle 1 will not penetrate the opposite boundary of blood vessel 200 when it is advanced through window 18 into blood vessel 200. Holder 90 supports blood vessel 200 during penetration and injection by the needle.

Again, the interior of body 15 may serve as reservoir R. Alternatively, reservoir R may be provided as a confined chamber either within body 15 or, preferably, with a section of its periphery constituting a part of the outer wall of the body 15. If such peripheral section is made from a flexible material, such flexibility could compensate for any volume changes in reservoir R. However, at least an injection port 61 should be provided to allow for refilling reservoir R.

A pump P connects reservoir R with an infusion needle 1 which is mounted on a drive unit D for both longitudinal and lateral displacement.

Pump P is driven by a first motor M and drive unit D is driven by a separate, second motor M. Alternatively, a single motor M may be used to drive both pump P and drive unit D. Also, as described above, actuation of pump P may simultaneously cause actuation of drive unit D. Alternatively, actuation of drive unit D may cause actuation of pump P.

A long-life battery B is provided to supply the two motors M with energy. Alternatively, an accumulator, such as a rechargeable battery, may be used instead of long-life battery B.

Furthermore, a control unit C is provided to control the two motors M. In the embodiment shown in FIG. 8, control unit C is programmable from outside the patient's body by means of an external data processing device 80. Data exchange between the data processing device 80 and control unit C is preferably wireless through an implanted data transmission interface for wirelessly transmitting data from outside the patient's body to the control unit C, but can be by wire through the patient's skin, if desired. Furthermore, data exchange is preferably bidirectional so as to also allow data transmission from control unit C to data processing device 80. Such data may include data on the performance of the device, number of infusion cycles performed, filling status of reservoir R and the like.

The infusion device in FIG. 8 further includes a feedback sensor F which—in the embodiment shown in FIG. 8—is placed in a blood vessel 200 to detect physiological parameters. Such parameters are fed to control unit C and might be used by a corresponding control program to prompt an infusion cycle. Alternatively or in addition, the physiological parameters may be transferred to external data processing device 80 and help the doctor in making a proper diagnosis. Eventually, the doctor will then use the data processing device 80 to adapt control unit C in accordance with the physiological parameters provided by feedback sensor F. Any kind of physical parameters of the patient or process parameters of the infusion device may be sent back to the control unit and the control unit may control the infusion device according to the results.

While FIG. 8 shows the third embodiment of the present invention with the infusion device being automatically driven and all components of the infusion device being contained within outer body 15, it should be understood that one or more of the various components may be implanted separate from outer body 15, such as battery B, or even outside the patient's body, such as control device C. Also, pump P and/or reservoir R may be connected separately to outer body 15, preferably attached thereto in close proximity. Components not specifically shown in FIG. 8 might be those as described in respect of the foregoing embodiments or might be different.

A method of treating a human being or an animal by implanting any one of the above described infusion devices in a patient's body comprises the steps of
cutting the skin,
free-dissecting a proper location for implantation of the infusion device within the patients body,
placing the infusion device at said proper location, and
closing at least the skin after placement of the infusion device.

Closing the skin may for instance include suturing, taping and other suitable techniques. The infusion device may be placed subcutaneously in the patient's body or within fat tissue or intramuscularly. In case it is placed adjacent a blood vessel (200) for injecting the infusion liquid directly into the circulating blood; the step of free-dissecting a proper location for implantation comprises free-dissecting the respective blood vessel and placing the infusion device adjacent the blood vessel. The blood vessel may then be secured to the infusion device by means of the holder 90 connected to the infusion device.

Alternatively, the infusion device may be placed within or adjacent the patient's gastro-intestinal or urinary tract. In the case of placing it adjacent the tract, again, it may be secured to the gastro-intestinal or urinary tract by means of a holder connected to the infusion device. As a further alternative, the infusion device may be placed in the patient's thorax or in the patient's abdomen.

Where the infusion device is placed adjacent a blood vessel or adjacent or within the patient's gastro-intestinal or urinary tract or within the patient's thorax or abdomen, the steps of cutting the skin, free-dissecting the proper location for implantation and placing the infusion device at said proper location may comprise:
where the infusion device is implanted in the patient's thorax or abdomen, inserting a Varess needle or another type of gas inflation needle into the abdomen or thorax cavity and filling the abdomen or thorax cavity with a gas,
cutting a key-hole,
inserting at least one trocar through the key-hole towards the proper location,
advancing one or more medical instruments and a camera through the at least one trocar towards said location,
dissecting said location, and
supplying the infusion device or part thereof to said location through the at least one trocar or through a separate incision in the skin.

For instance, the reservoir R may be placed in the abdomen or thorax cavity in the way described above. Alternatively, the infusion device or part thereof, such as the reservoir R, may be implanted by open surgery, in which case the thorax or abdominal wall is opened for placing the infusion device at the proper location within the patient's thorax or abdomen and, afterwards, the skin and other layers of tissue are closed, such as by suturing, and are preferably sutured in layers.

Replenishing of the reservoir R preferably comprises the step of injecting a volume of infusion liquid through an injection port connected to and/or integrated in the periphery of the reservoir.

One or more of the following elements of the infusion device may be implanted remote from at least drive unit D and infusion needle 1:
motor M for actuation of drive unit D,
energy storage means B to provide motor M with energy, comprising at least one of a battery, a capacitor and a rechargeable battery,
galvanic coupling elements 90 between either external energy source E or energy storage means B and motor M for transmitting energy to motor M in contacting fashion,
wireless coupling elements adapted to connect either motor M or energy storage means B or both to extra-corporal primary energy source E for transmitting energy to either motor M or energy storage means B or both in non-contacting fashion,
control unit C for controlling motor M,
wireless energy transmission or receiving means,
the data transmission interface for wirelessly transmitting data from external data processing device 80 to control unit C,
feedback sensor F,
reservoir R for holding the infusion liquid, and
injection port 61 for refilling the reservoir.

The invention claimed is:

1. An infusion device implantable in a patient's body, the infusion device comprising:
a body implantable in the patient's body and having an outer wall,
an infusion needle disposed within the body of the infusion device and having a tip end, and
a drive unit coupled to the infusion needle which advances and retracts the tip end of the infusion needle to penetrate any fibrosis surrounding the infusion device, when the infusion device is implanted in the patient's body,
said infusion needle and drive unit being implantable in the patient's body, the drive unit being operable when implanted in the patient's body,
wherein the infusion needle is disposed within the body of the infusion device with the tip end of the infusion needle being arranged for penetrating a penetration area in the outer wall, and wherein the drive unit further comprises an apparatus coupled to the infusion needle that laterally moves the tip end of the infusion needle within the body of the infusion device for variation of the injection site in the penetration area of the outer wall.

2. The infusion device of claim 1, wherein the infusion needle has a tube-like body closed at the tip end and having a laterally arranged delivery exit port.

3. The infusion device of claim 1, wherein a reservoir is coupled to the infusion needle.

4. The infusion device of claim 3, wherein at least a section of a periphery of the reservoir is made from a flexible material permitting volume changes of the reservoir by deformation of the flexible material as infusion liquid is filled into or drawn out of the reservoir.

5. The infusion device of claim 4, wherein the flexible material comprises a polymer membrane.

6. The infusion device of any of claim 5, wherein drawing of liquid from the reservoir causes a negative pressure in at least part of the reservoir.

7. The infusion device of any of claim 6, wherein the reservoir comprises a gas chamber and a liquid chamber, said chambers being separated by the polymer membrane.

8. The infusion device of claim 3, wherein the reservoir has an injection port for refilling the reservoir.

9. The infusion device of claim 8, wherein the injection port comprises a material which is self-sealing in respect of penetrations caused by a replenishing needle.

10. The infusion device of claim 3, wherein the infusion needle is disposed within a body of the device with the tip end of the infusion needle arranged for passing through an outer wall of said body and the reservoir is separate from the body of the device for remote implantation within a patient's body.

11. The infusion device of claim 3, wherein the reservoir is part of or is contained within the body of the device.

12. The infusion device of claim 11, wherein at least a section of a periphery of the reservoir at least partially constitutes the outer wall of the body of the device.

13. The infusion device of claim 3, wherein a pump is coupled to the reservoir for pumping infusion liquid from the reservoir to the infusion needle.

14. The infusion device of claim 13, wherein the pump comprises a valve device having a first and a second valve member, each of said first and second valve members having a smooth surface facing each other so as to form a sealing contact between the first and second valve members and further having different liquid channels that can be brought into alignment by displacement of the two smooth surfaces relative to one another while maintaining the sealing contact.

15. The infusion device of claim 14, wherein the first and second valve members are made from a ceramic material.

16. The infusion device of claim 13, wherein the pump is a membrane type pump.

17. The infusion device of claim 16, wherein the membrane type pump comprises a membrane displaceable by a piston as the piston moves, the piston being coupled to the valve device so as to slidably displace the first and second valve members relative to one another as the piston moves.

18. The infusion device of claim 13, wherein the pump is separate from the body of the device for remote implantation within a patient's body.

19. The infusion device of claim 13, wherein the pump is contained in the body of the device.

20. The infusion device of claim 1, wherein a reservoir is coupled to the infusion needle and a pump is coupled to the reservoir for pumping infusion liquid from the reservoir to the infusion needle, and wherein at least one motor is provided for actuation of at least one of the pump the drive unit and any other energy consuming part of the infusion device.

* * * * *